United States Patent
Hui et al.

(10) Patent No.: US 6,689,937 B2
(45) Date of Patent: Feb. 10, 2004

(54) TRANSGENIC MOUSE MODEL OF BASAL CELL CARCINOMA

(75) Inventors: Chi-Chung Hui, Toronto (CA); Andrzej A. Dlugosz, Ann Arbor, MI (US)

(73) Assignees: The Hospital for Sick Children, Toronto (CA); University of Michigan, Ann Arbor, MI (US)

( * ) Notice: Subject to any disclaimer, the term of this patent is extended or adjusted under 35 U.S.C. 154(b) by 32 days.

(21) Appl. No.: 09/758,937

(22) Filed: Jan. 11, 2001

(65) Prior Publication Data

US 2001/0027566 A1 Oct. 4, 2001

Related U.S. Application Data

(60) Provisional application No. 60/175,637, filed on Jan. 12, 2000.

(51) Int. Cl.$^7$ .................. G01N 33/00; A01K 67/027; C12N 15/00; C07H 21/02; C07H 21/04

(52) U.S. Cl. ..................... 800/3; 800/21; 800/25; 800/18; 536/23.1; 435/325

(58) Field of Search ............... 800/13, 18, 21, 800/25, 3; 536/23.1; 435/325

(56) References Cited

PUBLICATIONS

Wall R. J. Transgenic livestocks: progress and prospects for the future. 1996, Theriogenology 45: 57–68.*
Houdebine L. Production of pharmaceutical proteins from transgenic animals. 1994, J. Biotechnology 34: 269–287.*
Ebert K.M. A Moloney MLV–rat somatotropin fusion gene produces biologically active somatotropin in a transgenic pig. 1988, Mol. Endocrinol., 2: 277–283.*
Kappel C.A. Regulating gene expression in transgenic animals. 1992, Cur. Opin. Biotech., 3: 548–553.*
Hammer R. E. Genetic engineering of mammalian embryos. 1986, J. Amin. Sci. 63: 269–278.*
Strojek and Wagner. The use of transgenic animal techniques for livestock improvement. 1988, Plenum Press. Genetic Engineering: principles and methods, vol. 10, pp. 221–246.*
Sheng H. Dissecting the oncogenic potential of Gli2: deletion of an NH2–terminal fragment alters skin tumor phenotype. 2002 Cancer Research 62: 5308–5316.*
Landis et al. "Cancer Statistics, 1999," *CA Cancer J. Clin.* vol. 49, No. 1, pp. 8–31 (1999).
Dahmane et al. "Activation of the transcription factor *Gli1* and the Sonic hedgehog signalling pathway in skin tumours," *Nature.* vol. 389, pp. 876–881 (1997).
Unden et al. "Human patched (PTCH) MRNA is overexpressed consistently in tumor cells of both familial and sporadic basal cell carcinoma," *Cancer Research.* vol. 57, pp. 2336–2340 (1997).

Gailani et al. "The role of the human homologue of Drosophila patched in sporadic basal cell carcinomas," *Nat. Genet.* vol. 14, pp. 78–81 (1996).
Hahn et al. "Mutations of the human homolog of Drosophila patched in the nevoid basal cell carcinoma syndrome," *Cell.* vol. 85, pp. 841–851(1996).
Johnson, R.L. et al. "Human homolgo of patched, a candidate gene for the basal cell nevus syndrom," *Science.* vol. 272, pp. 1668–1671 (1996).
Van Ohlen et al. "Hedgehog signaling regulates transcription through cubius interruptus, a squence–specific DNA binding protein," *Proc. Natl. Acad. Sci. USA.* vol. 94, pp. 2404–2409 (1997).
Alexandre, C. et al. "Transcriptional activation of hedgehog target genes in Drosphila is mediated directly by the cutitus interruptus protein, a member of the GLI family of zinc finger DNA–binding proteins," *Genes Dev.* vol. 10, pp. 2003–2013 (1996).
Altaba, A. "Gli proteins and hedgehog signaling: development and cancer," *Trends Genet.* vol. 15, pp. 418–425 (1999).
Hynes, et al. "Control of cell pattern in the neural tube by the zinc finger tanscription factor and oncogene Gli–1," *Neuron.* vol. 19, pp. 15–26 (1997).
Lee, J. et al. "Gli1 is a target of Sonic hedgehog that induces ventral neural tube development," *Development.* vol. 124, pp. 2537–2552 (1997).
Matise et al. "*Gli2* is required for induction of floor plate and adjacent cells, but not most ventral neurons in the mouse central nervous system," *Development.* vol. 125, pp. 2759–2770 (1998).
Oro, et al. "Regulation of Shh target gene expression plays a critical role in hair follicle and BCC formation (abstract)," *J. Invest. Dermatol.* vol. 112, p. 525 (1999).
Ding, Q. et al. "Diminished Sonic hedgehog signaling and lack of floore plate differentiation in *GLI2* mutant mice," *Development.* vol. 125, pp. 2533–2543 (1998).
Hardcastle, et al. "The Shh signalling pathway in tooth development: defects in *Gli2* and *Gli3* mutants," *Development.* vol. 125, pp. 2803–2811 (1998).
Motoyama, et al. "Essential function of *Gli2* and *Gli3* in the formation of lung, trachea and oesophagus," *Nat. Genet.* vol. 20, pp. 54–57 (1998).
Lavker, R.M. et al. "Hair follicle stem cells: their location, role in hair cycle, and involvemtn in skin tumor formation," *J. Invest. Dermatol.* vol. 101, pp. 16S–26S (1993).

(List continued on next page.)

*Primary Examiner*—Peter Paras, Jr.
(74) *Attorney, Agent, or Firm*—Myers Bigel Sibley & Sajovec, P.A.

(57) ABSTRACT

The present invention provides transgenic non-human animal models of basal cell carcinoma which allows for the characterization of the disease as well as for providing a system for the development and testing of potential treatments.

9 Claims, 4 Drawing Sheets

OTHER PUBLICATIONS

Ramirez, et al. "Sequences 5' of the bovine keratin 5 gene direct tissue–and cell–type–specific of a lacZ gnene in the adult and during development," *Differentiation*. vol. 58, pp. 53–64 (1994).

McGowan, K.M. and Coulombe, P.A. Onset of keratin 17 expression coincides with the definition of major epithelial lineages during skin development. *J. Cell Biol*. vol. 143, pp. 469–486 (1998).

Markey, A.C. et al. "Keratin expression in basal cell carcinomas," *Br. J. Dermatol*. vol. 126, pp. 154–160 (1992).

Smoller, B.R. et al. "bcl–2 expression reliably distinguishes trichoepitheliomasfrom basal cell carcinomas," *Br. J. Dermatol*. vol. 131, pp. 28–31 (1994).

Yoshikawa K. et al. "Biochemical and immunohistochemical analyses of keratin expression in basal cell carcinoma," *J. Dermatol. Sci*. vol. 17, pp. 15–23 (1998).

Nagano, T. et al. "Overexpression of the human homologue of Drosophila patched (PTCH) in skin tumors: specifically for basal cell carcinoma," *Br. J. Dermatol*. vol. 140, pp. 287–290 (1999).

Kallasy, M. et al. "Patched (ptch)–associated preferential expression of smoothened (smoh) in human basal cell carcinoma of the skin," *Cancer Res*. vol. 57, pp. 4731–4735 (1997).

Green, J. et al. "Basal cell carcinoma development is associated with induction of the expression of the transcription factor Gli–1," *Br. J. Dermatol*. vol. 139, pp. 911–915 (1998).

Oro, A.E. et al. "Basal cell carcinomas in mice overexpressing sonic hedgehog," *Science*. vol. 276, pp. 817–821 (1997).

Xie, J. et al. "Activating smoothened mutations in sporadic basal–cell carocinoma," *Nature*. vol. 391, pp. 90–92 (1998).

Aszterbaum, M et al. "Ultraviolet and ionizing radiation enhance the growth of BCC and trichoblastomas in patched heterozygous knockout mice," *Nat. Med*. vol. 5, pp. 1285–1291 (1999).

Chiang, C. et al. "Essential rold for sonic hedgehog during hair follicle morphogenesis," *Dev. Biol*. vol. 205, pp. 1–9 (1999).

Tarutani, M. et al. "Tissue–specific knockout of the mouse Pig–a gene reveals important roles for GPI–anchored proteins in skin development," *Proc. Natl. Acad. Sci. USA*. vol. 94, pp. 7400–7405 (1997).

Sasaki, H. et al. "Regulation of *Gli2* and *Gli3* activities by an amino–terminal repression domain: implication of *Gli2* and *Gli3* as primary mediators of Shh signaling," *Development*. vol. 126, pp. 3915–3924 (1999).

Lobe, C.G., et al. "Z/AP a double reporter for Cre–mediated recombination," *Dev. Biol*. vol. 208, pp. 281–292 (1999).

Mo, R. et al. "Specific and redundant functions of *Gli2* and *Gli3* zinc finger genes in skeletal patterning and development," *Development*. vol. 124, pp. 113–123 (1997).

\* cited by examiner

SEQUENCE LISTING

<160> NUMBER OF SEQ ID NOS: 18

<210> SEQ ID NO 1
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 1
tgcatataaa ttctggctgg cg                                           22

<210> SEQ ID NO 2
<211> LENGTH: 23

```
<212> TYPE: DNA
<213> ORGANISM: Artificial sequence
<220> FEATURE:
<223> OTHER INFORMATION: Synthetic oligonucleotide

<400> SEQUENCE: 2
gcatgaacat ggttagcaga ggg                                          23

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
acaaggacga cgatgacaag                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
agacccctct ctttcagatg                                              20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
gtcggaagtc ctattcacgc                                              20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
cagtctgctc tcttccctgc                                              20

<210> SEQ ID NO 7
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 7
gagcagaagc ccttcaag                                                18

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8
```
gacagtcttc acatgctt                                      18

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
caagcctgat gaagacctcc                                    20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
gctttgaacg gtttctgctc                                    20

<210> SEQ ID NO 11
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 11
aacaaaaatt caaccaaacc tc                                 22

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
tgtcttcatt ccagttgatg tg                                 22

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
tgcctctctg gagggcttcc                                    20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cagttcctcc tgccagtgca                                    20

<210> SEQ ID NO 15
<211> LENGTH: 21
<212> TYPE: DNA
<213> ORGANISM: Artificial sequence

```
<220> FEATURE:
<223> OTHER INFORMATION: Synthetic oligonucleotide

<400> SEQUENCE: 15
taccacaggc attgtgatgg a                                              21

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 16
caacgtcaca cttcatgatg g                                              21

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
tctgtgatga accagtggcc                                                20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
gccacggagt tctctgcttt                                                20
```

TRANSGENIC MOUSE MODEL OF BASAL CELL CARCINOMA

RELATED APPLICATIONS

This application claims priority from U.S. patent application Ser. No. 60/175,637 filed Jan. 12, 2000.

FIELD OF THE INVENTION

The present invention relates to transgenic non-human animal models of basal cell carcinoma. More specifically, the present invention is directed to mouse models of basal cell carcinoma allowing for the characterization of the mechanism of the disease as well as for developing and testing potential treatments.

BACKGROUND OF THE INVENTION

Throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure.

Approximately 1,000,000 epithelial skin cancers are diagnosed in the United States each year[1], and the great majority of these are basal cell carcinomas (BCCs). The pathogenesis of these tumors involves constitutive activation of the Sonic hedgehog (Shh) signaling pathway[2–4]. In many BCCs this can be attributed to loss-of-function mutations involving PTCH1[5,6], which encodes a SHH receptor and antagonist. However, the identity of the specific downstream effector in the Shh pathway leading to cancer development remains unknown.

It is now demonstrated that transgenic mice overexpressing the transcription factor Gli2 in cutaneous keratinocytes develop multiple skin tumors that are grossly indistinguishable from human BCCs. These tumors express the same protein markers as human BCCs and exhibit strikingly elevated levels of Ptch1 and Gli1, a hallmark of human BCCs but not squamous tumors. These results establish Gli2 as a potent oncogene in skin and suggest a pivotal role for this transcription factor in the development of BCC, the most common cancer in humans.

With the development of transgenic animal models for basal cell carcinoma potential treatments including effective drug therapies can now be developed and tested.

SUMMARY OF THE INVENTION

The present invention provides transgenic non-human models of basal cell carcinoma and more specifically transgenic mouse models of basal cell carcinoma which allows for the characterization of the disease as well as for providing a system for the development and testing of potential treatments. In particular the invention provides transgenic mice overexpressing the transcription factor Gli2 in cutaneous keratinocytes which leads to the development of multiple skin tumors that are grossly indistinguishable from human BCCs. The present invention also provides methods for the production of non-human transgenic animal models of basal cell carcinoma as well as methods for testing compounds for an effect on basal cell carcinoma. The invention also encompasses isolated cells from the transgenic animal models as well as isolated eggs of the transgenic animals.

In accordance with the present invention there is provided a transgenic non-human animal model for basal cell carcinoma.

In accordance with another aspect of the present invention is a transgenic mouse model for basal cell carcinoma. The basal cell carcinoma as developed by the transgenic models physiologically resembles that of human basal cell carcinoma.

According to an aspect of the invention is a transgenic mouse model characterized by having a great similarity to several physiological conditions existing in naturally occurring human basal cell carcinoma, based on the expression of keratin 17 (K17), Bcl-2, keratin K5 and the non-expression of keratin K1 and keratin K6 as well as on histological analysis. Furthermore, the basal cell carcinoma tumors developed by the transgenic mice also express the same protein markers as human basal cell carcinomas as well as elevated levels of $Ptch_1$ and Gli1.

According to another aspect of the invention is a transgenic mouse whose genome contains at least one copy of a Gli2 nucleotide sequence wherein said mouse develops basal cell carcinoma. The nucleotide sequence may be genomic DNA, cDNA or RNA.

According to a further aspect of the invention is a transgenic mouse whose somatic and germ cells comprise a Gli2 nucleotide sequence, wherein the expression of said sequence leads to the development of basal cell carcinoma.

In accordance with a first embodiment of the invention, a construct comprising a full-length mouse Gli2 cDNA with an amino-terminal FLAG tag under the control of a bovine keratin 5 (K5) promoter and also containing a rabbit ℘-globin intron 2 sequence and an SV40 polyA signal was made. The construct was then introduced into mouse embryos using standard techniques such as microinjection. Founders were identified and any skin tumors identified and biologically characterized.

In accordance with a further embodiment of the invention, a binary transgenic system was utilized to target Gli2 overexpression in keratinocytes. In this approach, a Gli2 transgene was placed downstream of a βgeo (lacZ/neomycin) cassette flanked by a pair of loxP sites. Upstream of the βgeo cassette was placed a strong ubiquitous promoter such as the βactin promoter. This construct was used to create Z/AP-Gli2 mice in which lacZ expression was driven in all cells. In this system, the Gli2 transgene is activated only when the βgeo cassette is excised by Cre recombination. For Gli2 overexpression, the Z/AP-Gli2 mice were crossed with a K5-Cre transgenic line producing K5-Cre:Z/AP-Gli2 mice having a high incidence of basal cell carcinoma. Furthermore, in initial experiments, Cre was electroporated into ES cell clones containing epitope tagged Gli2 or Gli2ΔN and chimeric mice generated by aggregration of ES cells with morula stage mouse embryos. Z/AP-Gli2 and Z/AP- Gli2ΔN mouse lines were established after germline transmission.

Animal cells can be isolated from the transgenic mice or prepared using the same constructs with standard techniques such as lipofection or electroporation. The transgenic animals or animal cells may then used to screen for compounds altering the pathological course of basal cell carcinoma leading to the development of pharmaceutical therapeutic approaches for treating the disease.

In accordance with a further aspect of the present invention is a transgenic mouse whose somatic and germ cells comprise a nucleic acid construct wherein the construct comprises a nucleic acid encoding Gli2 under the control of a suitable promoter and wherein the construct is transcribed. The construct may additionally contain any suitable polyA elements as well as a suitable regulatory element in order to enhance the expression of the Gli2 transgene.

In one embodiment of the invention the nucleic acid encoding Gli2 is a full length mouse cDNA with an amino-terminal FLAG tag operatively linked to a bovine keratin 5 (K5) promoter. In a further embodiment of the invention such construct further comprises a rabbit ℘-globin intron 2 sequence and an SV40 polyA signal.

In another embodiment of the invention the nucleic acid encodes amino acids 280-1544 of Gli2 (herein referred to as Gli2ΔN). In a further embodiment, the nucleic acid of the invention encodes Gli2 or a fragment or variant thereof which leads to Gli2 expression.

In accordance with still a further aspect of the present invention is a transgenic mouse whose somatic and germ cells comprise a nucleic acid construct wherein the construct comprises a full-length mouse Gli2 cDNA or variant thereof with an amino-terminal FLAG tag operatively linked to a bovine keratin 5 (K5) promoter and also containing a rabbit ℘-globin intron 2 sequence and an SV40 polyA signal, and wherein the nucleic acid is expressed in skin cells of the transgenic mouse.

In accordance with another aspect of the present invention is a transgenic mouse whose somatic and germ cells comprise a nucleic acid construct wherein the construct comprises a full-length mouse Gli2 cDNA or variant thereof operatively linked to a βactin promoter. The Gli2 transgene is activated by Cre recombination leading to expression of the Gli2 nucleic acid sequence in skin cells of the transgenic mouse such that the mouse develops basal cell carcinoma.

In accordance with still a further aspect of the present invention is a transgenic mouse whose somatic and germ cells comprise a nucleic acid construct wherein the construct comprises a full-length mouse Gli2 cDNA or variant thereof operatively linked to a bovine keratin 5 (K5) promoter and also containing a rabbit ℘-globin intron 2 sequence and an SV40 polyA signal, and wherein the nucleic acid is over expressed in skin cells of the transgenic mouse such that the transgenic mouse develops basal cell carcinoma.

In yet further aspects, the invention features methods for using the non-human transgenic animals, cells and cell lines of the invention for investigating molecular and cellular mechanisms of Gli2 mediated pathogenesis leading to the development of basal cell carcinoma.

In accordance with yet a further embodiment of the present invention is a method of testing compounds for an effect on basal cell carcinoma, the method comprising:

administering the compound to be tested to a transgenic mouse whose genome comprises a nucleic acid construct, wherein the construct comprises nucleic acid encoding a Gli2 oncogene or variant thereof operably linked to a suitable promoter and wherein the transgenic mouse develops basal cell carcinoma; and comparing one or more characteristics of the basal cell carcinoma tumors in the transgenic mouse to which the compound was administered with the same one or more characteristics of the tumors in the transgenic mouse to which the compound has not been administered, wherein a difference in one or more of the one or more characteristics indicates that the compound has an effect on basal cell carcinoma.

In accordance with still another embodiment of the present invention there is provided a method of identifying markers associated with basal cell carcinoma, the method comprising:

comparing the presence, absence or level of expression of genes in skin tissue from a transgenic mouse and skin tissue from a second mouse, wherein the genome of the transgenic mouse comprises a nucleic acid construct and the genome of the second mouse does not comprise the nucleic acid construct, wherein the construct comprises nucleic acid encoding a Gli2 oncogene or variant thereof operably linked to a suitable promoter, and wherein the nucleic acid is expressed in the skin cells of the transgenic mouse such that the transgenic mouse develops basal cell carcinoma, wherein the difference between the transgenic mouse and the second mouse in the presence, absence or level of expression of a gene indicates that the expression of the gene is a marker associated with basal cell carcinoma.

In accordance with a further embodiment of the present invention are in vitro cell culture models for developing methods of treatment including the identification of therapeutically active agents for basal cell carcinoma, wherein the cells contain a nucleic acid construct comprising a nucleic acid encoding a Gli2 oncogene or variant thereof under the control of a suitable promoter and wherein the nucleic acid is expressed in the cells. Therapeutically active agents may include for example but are not limited to small molecule drugs including peptides and peptidomimetic drugs.

In accordance with a further embodiment of the present invention is a transgenic cell comprising a nucleic acid encoding a Gli2 oncogene or variant thereof operably linked to a suitable promoter and wherein the nucleic acid is expressed in the transgenic cell.

In accordance with yet another aspect of the present invention is a transgenic cell comprising a nucleic acid construct wherein the construct comprises a full-length Gli2 cDNA operatively linked to a bovine keratin 5 (K5) promoter and wherein the nucleic acid is expressed in the cells. The construct may further comprise a regulatory element to enhance expression of the transgene such as a rabbit ℘-globin intron 2 sequence and also may contain a suitable polyA element such as a SV40 polyA signal. Such transgenic cells may be used in various assays to screen for compounds which are therapeutically effective against the disease.

In accordance with a further aspect of the present invention is a plasmid insert comprising a nucleic acid encoding a Gli2 oncogene or variant thereof under the control of a suitable promoter. Such plasmid insert being insertable in a mammalian genome in order to over express Gli2 in the desired cells, wherein such overexpression leads to the development of basal cell carcinoma. Preferably, the insert comprises a full-length Gli2 cDNA under the control of a keratin 5 (K5) promoter.

In accordance with another aspect of the present invention is a transgene construct comprising a nucleic acid encoding a Gli2 oncogene downstream of a βgeo cassette flanked by a pair of loxP sites. Downstream of the βgeo cassette are polyadenylation sites and upstream of the βgeo cassette is a ubiquitous promoter. The transgene is activated by excision of the βgeo cassette by Cre recombination.

In accordance with yet a further aspect of the present invention is the use of a Gli2 oncogene or variant thereof in a mammal in order to stimulate basal cell carcinoma development in said mammal.

In accordance with yet a further aspect of the present invention is the use of a Gli2 oncogene or variant thereof in a mammal in order to stimulate Shh target genes in said mammal.

In accordance with still a further aspect of the invention is the use of the Gli2 oncogene or variant thereof in a construct, such construct being insertable into a mammalian genome, wherein the Gli2 oncogene is expressible and stimulates basal cell carcinoma development.

BRIEF DESCRIPTION OF THE DRAWINGS

The present invention will be further understood from the following description with reference to the Figures, in which.

Figure 1:
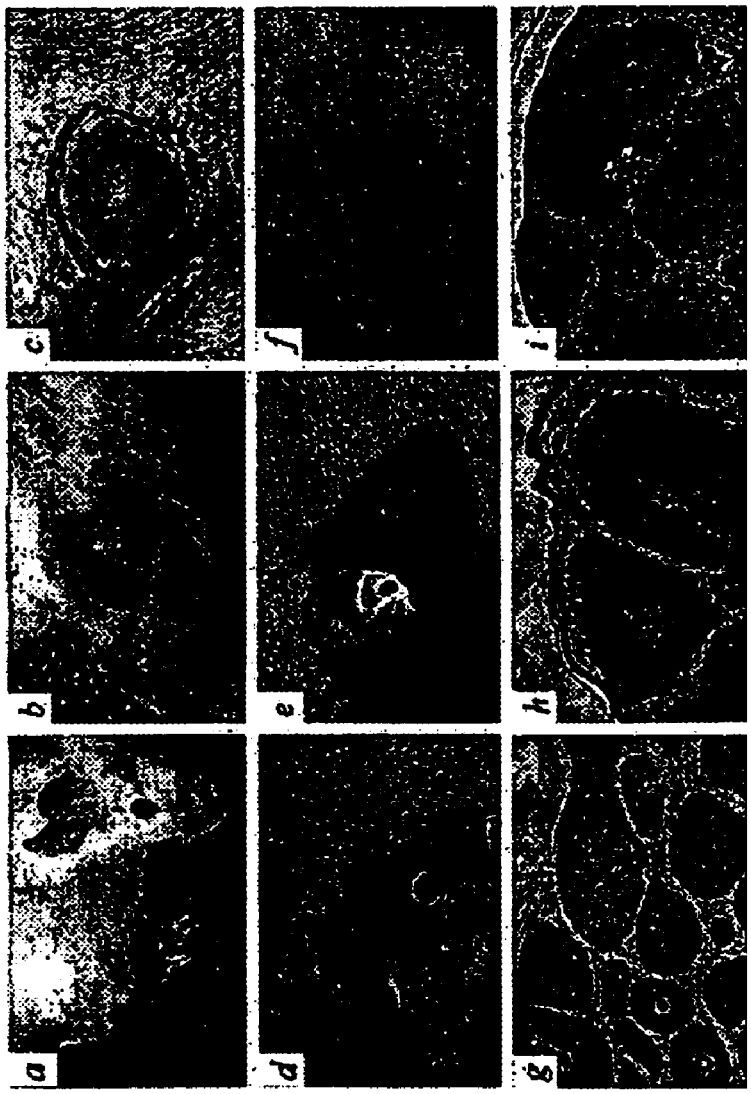
FIG. 1, panels (a) through (i), show photographs illustrating that K5-Gli2 transgenic mice develop multiple BCCs. Panels (a,b,d,e) show the gross appearance of tumors on K5-Gli2 founders compared to human BCC, panel (c) and pigmented BCC, panel (f). Typical features seen in non-pigmented BCCs in both species include a smooth, shiny surface; pearly or translucent appearance; and prominent telangiectases, panels (a–c). Ulceration, seen in some of the K5-Gli2 tumors [note lesions below eye in panel (e)], is also observed in human BCCs, panel (f). Pigmented BCCs in humans, panel (f) and K5-Gli2 mice, panel (e) appear to grossly resemble malignant melanoma. Histology of mouse panels (g,h) and human panel (i) BCC. Tumors in both species are composed of masses of monomorphous cells, with scant cytoplasm, filling the dermis. Note the brown-black melanin in pigmented tumors, panels (g,i), and striking similarity in the appearance of mouse BCC in panel (h) and human BCC in panel (i).

In the drawings, preferred embodiments of the invention are illustrated by way of example. It is to be expressly understood that the description and drawings are for the purpose of illustration and as an aid to understanding, and are not intended as a definition of the limits of the invention.

DETAILED DESCRIPTION OF THE PREFERRED EMBODIMENTS

It has now been demonstrated that Gli2, a transcription factor, is an oncogene in skin involved in the development of basal cell carcinoma in humans. This has been demonstrated through the development of transgenic mouse models for human basal cell carcinoma that can now be used to further characterize the disease as well as provide a system for testing potential treatments.

The GLI transcription factor cubitus interruptus plays a central role in responses to Drosophila Hedgehog[7,8] leading to a focus on the vertebrate GLI proteins (Gli1, Gli2, and Gli3)[9] as potential mediators of Shh signaling. Gli1 expression levels correlate with Shh pathway activity under normal and pathologic conditions, and ectopically-expressed Gli1 can mimic responses to Shh in certain settings[10,11]. However, Gli1−/− mice are phenotypically normal[12], and transgenic mice overexpressing Gli1 in skin do not develop BCCs[13]. In contrast, Gli2−/− mice exhibit developmental defects in several organ systems[12,14–16] including their skin, which contains hypoplastic hair follicles (R. Mo et al. in preparation). Coupled with the notion that BCCs are derived from hair follicles[17], these findings prompted the exploration of the potential involvement of Gli2 in BCC development.

In a first embodiment of the invention, a full-length mouse Gli2 cDNA was targeted to the skin of transgenic mice using a bovine keratin 5 (K5) promoter, which is active in keratinocytes of the epidermal basal layer and outer root sheath of hair follicles[18]. Three of five founders developed conspicuous skin tumors by three months of age (FIG. 1). The distribution of tumors was similar in these animals, involving the tail and at least one ear or paw in each animal. In two of the mice, lesions were also present on the face, and two animals had multiple tumors on the trunk. Examination of tumors on the albino founder revealed several features characteristic of human BCCs: a smooth and shiny surface, translucent or pearly appearance, and prominent telangiectases (FIGS. 1a–c). Ulceration, also typical for human BCCs, was seen in several lesions on each of these animals. The majority of tumors on the agouti and black mice were pigmented and bore a strong resemblance to human pigmented BCCs (FIGS. 1d–f). None of the tumors exhibited evidence of hyperkeratosis, a prominent feature of squamous cell carcinomas arising in human or rodent skin.

Histological analysis strongly supported the clinical diagnosis of BCC (FIGS. 1g–i). Tumors were composed of large masses of monomorphous cells with scant cytoplasm arranged as nests scattered throughout the dermis. Dilated blood vessels were seen in the stroma between the tumor and overlying epidermis. Pigmented tumors contained brown melanin deposits scattered among the tumor cells or in the stroma, similar to findings in human pigmented BCCs. Small tumors were occasionally seen replacing the upper portion of hair follicles, consistent with the proposed origin of human BCCs[17]. In some of the K5-Gli2 tumors, keratinocytes at the periphery of tumor islands were arranged in a palisading pattern similar to that described in human BCCs. Mitotic activity was low in most of the tumors, which remained localized without evidence of infiltration into deeper tissues.

Figure 2:
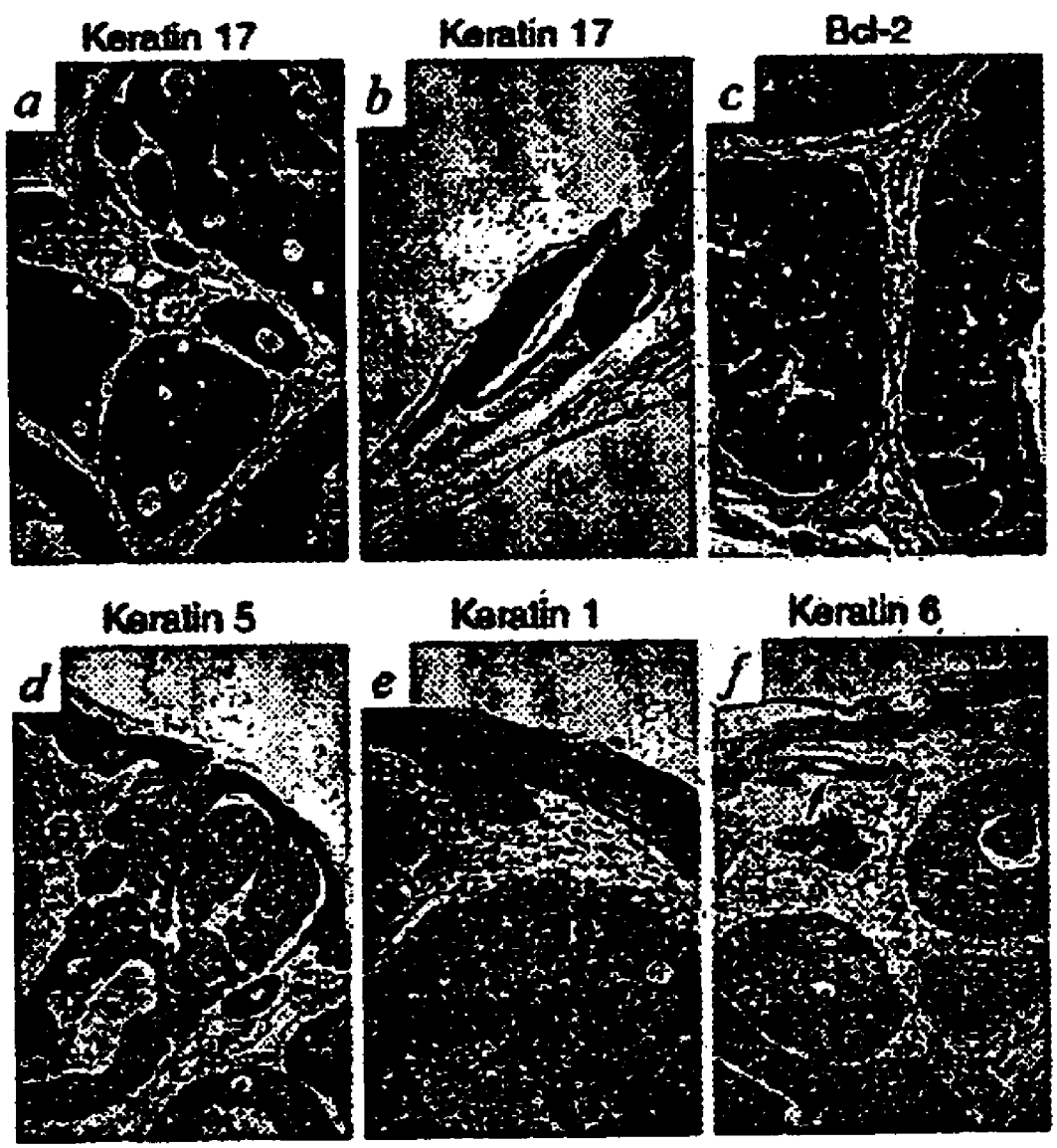
FIG. 2, panels (a) through (f), shows immunohistochemical photographs of tumors from K5-Gli2 transgenic mice supporting a diagnosis of BCC. Keratin 17, expressed in the outer root sheath of hair follicles and human BCCs, is detected in tumors from K5-Gli2 mice, panels (a,b). Microscopic tumors were occasionally seen replacing the upper portion of hair follicles, panel (b). Bcl-2 is a reliable marker for human BCCs and is also expressed throughout tumor masses from K5-Gli2 mice, panel (c). The basal cell keratin K5 is expressed in K5-Gli2 skin tumors, panel (d), while the differentiation marker keratin 1 is expressed in suprabasal cells of epidermis but not tumor cells, panel (e). Keratin 6, which is expressed in squamous cell tumors but not BCCs, is also not detected in K5-Gli2 skin tumors, panel (f). Note K6 immunostaining in hair follicle [arrow in panel (f)] a normal site of expression for this keratin. The brown pigment scattered throughout tumor mass in panel (f) is melanin.

Immunohistochemical studies further strengthened the notion that tumors arising in K5-Gli2 transgenic mice are BCCs. Tumors expressed abundant keratin 17 (K17) even at their earliest stages of development (FIGS. 2a,b). K17 is not present in normal epidermis but is consistently expressed in both the outer root sheath of hair follicles[19] and human BCCs[20]. The mouse BCCs also expressed Bcl-2 (FIG. 2c), a useful marker that helps distinguish between BCCs and other epithelial skin tumors[21]. The basal cell keratin K5 was also expressed in tumors although at a lower level than in overlying epidermis (FIG. 2d). The differentiation-specific keratin K1, expressed in suprabasal spinous layers of normal epidermis but not human BCCs[20,22], was also not detected in the undifferentiated tumors from K5-Gli2 transgenic mice (FIG. 2e). Finally, keratin 6, which is present in human and rodent squamous cell tumors and epidermal hyperplasias but not human BCCs, was also undetectable in tumors from K5-Gli2 mice (FIG. 2f). Thus, the expression profile of multiple protein markers is identical in murine and human BCCs.

Figure 3:
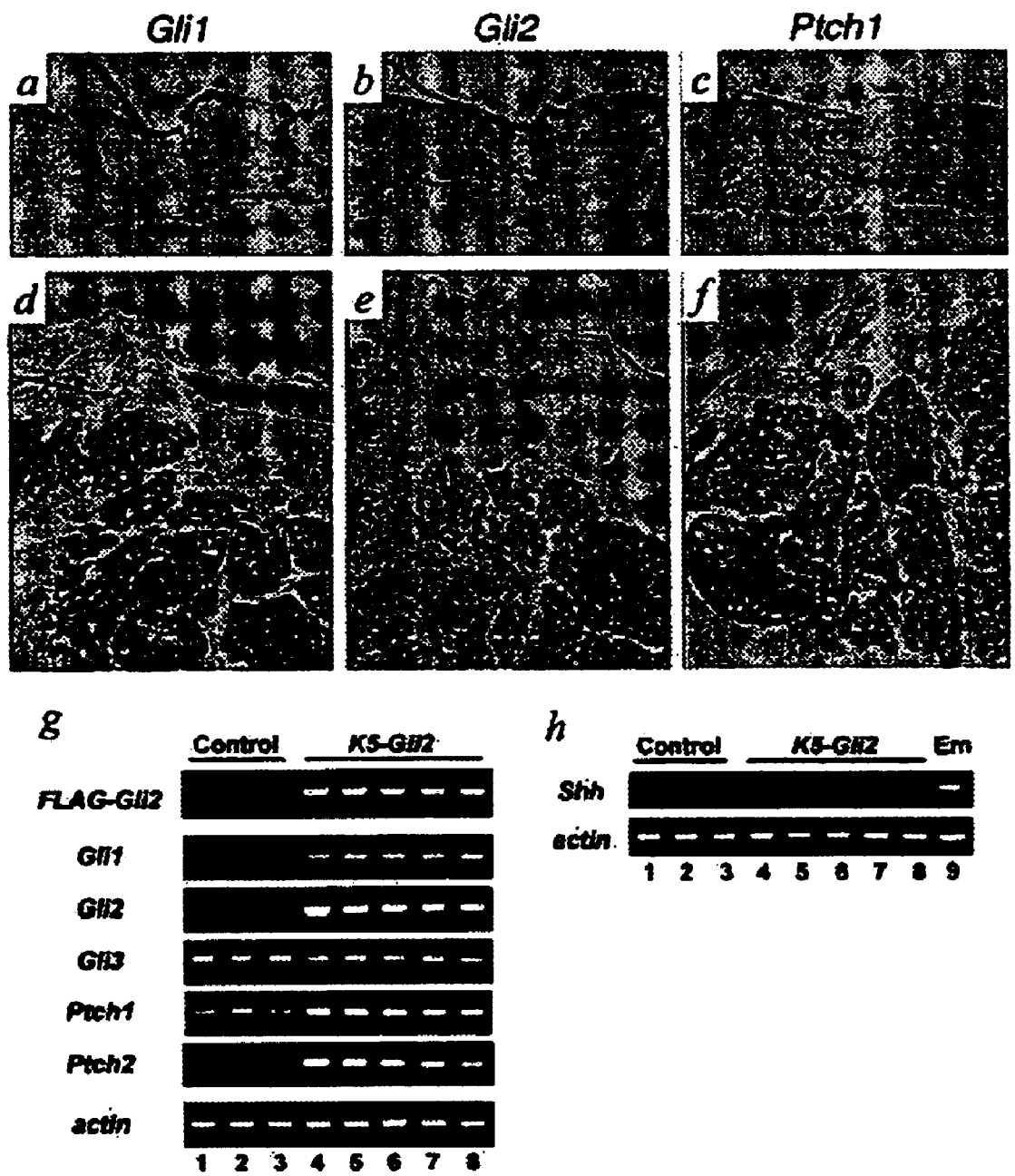
FIG. 3, panels (a) through (f), show photomicrographs illustrating the up-regulation of Shh target genes in skin tumors from K5-Gli2 transgenic mice. In situ analysis of sections from age-matched control skin, panels (a–c) and tumors from K5-Gli2 transgenic mice, panels(d–f), hybridized with the indicated riboprobes. Expression of Gli1, Gli2, and Ptch1 is strikingly elevated in tumor cells, panels (d–f), but is below the level of detection in control tissue, panels (a–c). Note that the riboprobe used to detect Gli2 transcripts does not distinguish between endogenous and transgenic Gli2 mRNA. Panel (g) shows RT-PCR analysis of RNA isolated from three control skin samples (lanes 1–3) and five transgenic skin-tumor samples (lanes 4–8) (g). Amplification using a primer pair to detect mRNA encoding FLAG-tagged Gli2 (FLAG Gli2) confirms transgene expression in tumor samples. Upregulation of Gli1, Gli2, Ptch1, and Ptch2 transcripts in tumors relative to control skin. Note similar expression of Gli3 in control skin and tumors, consistent with findings reported in human BCCs. Shh expression was not increased in RNA from K5-Gli2 transgenic skin tumors relative to control skin (h). Lane 9 contains RNA isolated from E18.5 mouse skin as a positive control for Shh.

Additional analysis of tumors from K5-Gli2 mice focused on Shh target genes, which are consistently upregulated in human BCCs but not squamous tumors[2,23,24]. In situ hybridization revealed abundant Gli1, Gli2, and Ptch1 mRNA in tumor cells, but not in overlying epidermis or age-matched control skin (FIGS. 3a–f). RT-PCR was performed using RNA isolated from K5-Gli2 transgenic tumors and skin from age-matched control mice (FIG. 3g). Primers specific for the FLAG-tagged Gli2 mRNA produced a band only in tumor samples, confirming transgene expression at the RNA level. There was also an increase in the expression of Gli1, Ptch1, and Ptch2 mRNA in tumors (FIG. 3g). No significant differences between Gli3 mRNA levels were noted in control and tumor samples, consistent with previous reports showing upregulation of Gli1 but not Gli3 in human BCCs[25]. There was also no detectable increase in the level of Shh mRNA (FIG. 3h), indicating that tumor development was not an indirect result of Gli2-mediated induction of Shh. These results indicate that overexpression of Gli2 in skin is sufficient for the activation of multiple Shh target genes, and provide evidence that tumors arising in K5-Gli2 mice are BCCs.

Figure 4:
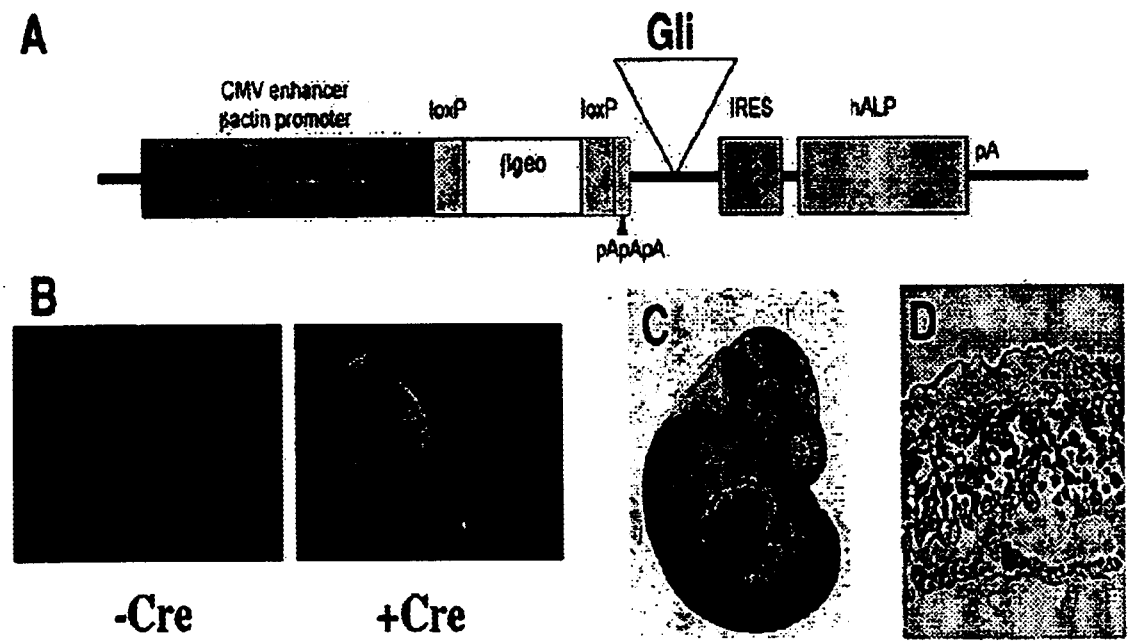
FIG. 4, panel (a) shows the Z/AP transgenic construct. Panel (b) shows immunostaining of FLAG-Gli2 in Z/AP-Gli2 embryonic stem cells upon βgeo cassette excision in embryonic stem cells. −Cre and +Cre indicate control and Cre-transfected cells, respectively. Panel (c) shows X-gal staining of E10.5Z/AP-Gli2 mouse embryos showing near ubiquitous lacZ expression. Panel (d) shows X-gal staining of skin section from a six week old Z/AP-Gli2 mouse showing high levels of lacZ expression in hair follicles.

In a further embodiment of the invention, a Cre-loxP based binary transgenic approach (Z/AP) was also employed to produce Z/AP-Gli2 and Z/AP-Gli2ΔN lines. The transgene construct is shown in FIG. 4(a). Using this approach Gli2 expression could be detected upon βgeo cassette (lacZ/neomycin) excision in embryonic stem cells (FIG. 4(a)) and Z/AP-Gli2 embryos showed ubiquitous lacZ expression (FIG. 4(c)). In adult skin, strong lacZ expression was detected in the hair follicles and interfollicular epidermis of the Z/AP-Gli2 and Z/AP-Gli2ΔN mice (FIG. 4(d)).

Specifically, the above noted Z/AP-Gli2 and Z/AP-Gli2ΔN mouse lines were generated by embryonic stem (ES) cell mediated transgenesis[31] in which Gli2 and Gli2ΔN cDNAs were inserted into the pCCALL vector[32] and these constructs were electroporated into ES cells[33]. ES cell clones with high level of lacZ expression were obtained by G418 selection and screened by Xgal-staining. Subsequently, single copy integrations were identified by Southern blot analysis. Cre-dependent expression of the Gli2 and Gli2ΔN transgenes were verified by electroporating Cre into these ES cell clones and immunostaining of epitope-tagged Gli2 and Gli2ΔN using an antibody against the FLAG epitope in the transfected cells. Chimeric mice were then generated by aggregration of ES cells with morula stage mouse embryos, and Z/AP-G/i2 and Z/AP-Gli2ΔN mouse lines were established after germline transmission[33].

This binary transgenic approach is useful for targeting Gli2overexpression in keratinocytes. The ES cell experiments were important to confirm that the βgeo stop cassette can be excised by Cre expression which was important to demonstrate prior to the generation of the Z/AP mice. Rather than electroporating Cre into ES cell clones it is also desirable to cross the Z/AP-Gli2 mice with a well-characterized K5-Cre transgenic line[30] in order to provide K5-Cre:Z/AP-Gli2 mice which have a high incidence of basal cell carcinomas similar to those observed in the K5-Gli2 transgenic founders. This approach also involves the use of Gli2Δ (amino acids 280-1544) which is a hyperactive form of Gli2 and appears to function without active Shh signaling[31]. Using this altered approach also allows for the systemic characterization of Gli2ΔN-induced skin tumorigenesis.

Previous transgenic models have established a role for Shh signaling in BCC development by activating this pathway at a proximal level. Skin-targeted expression of Shh[26] or a constitutively activate mutant of SMO[27], which is normally repressed by PTCH1, results in replacement of large regions of skin with BCC-like growths during late embryogenesis. Postnatal analysis of these mice has not been reported. In the case of Shh-overexpressors this is not feasible due to a perinatal lethal phenotype. More recently, BCC development was noted in adult (>9 month-old) Ptch +/− mice following exposure to UV or gamma radiation[28]. However, clinically-evident skin tumors were not observed in unirradiated Ptch +/− mice. Thus, the K5-Gli2 transgenic mice and the K5-Cre:Z/AP-Gli2ΔN mice now developed and described represent the first animal models of spontaneous BCC development in adult animals.

Shh signaling is activated in nearly all BCCs examined and yet mutations in PTCH1 or SMO have been reported in only a fraction. This suggests that alterations involving other molecules in the Shh pathway may underlie a proportion of these tumors. Regardless of the proximal defect that leads to uncontrolled Shh signaling in BCCs, Gli2 appears to play a central role in the genesis of these tumors. Consistent with this concept, we have now found that Gli2 is expressed in human BCCs. Although Gli2 was seen to be expressed in human BCCs[9], its role was not clearly established or understood and thus one would have not predicted that this oncogene could reliably be expressed in animal models resulting in BCC. Therefore, the role of this transcription factor in BCC development was never before established.

The presently developed transgenic mice enable the analysis and ellucidation of functional interactions between Shh components in a biologically relevant setting, and serve as a powerful model for evaluating the efficacy of mechanism-based therapeutic agents targeting this signaling pathway. The transgenic mice of the present invention will also allow for the development of various treatments for basal cell carcinoma including the identification of various therapeutically active agents including but not limited to other proteins, peptides, peptidomimetic drugs, small molecule drugs, chemicals and nucleic acid based agents.

While the present invention provides for the production of transgenic mouse models of basal cell carcinoma, it is understood by those skilled in the art that the present invention, in general, provides non-human animal models of human basal cell carcinoma. Such transgenic models provide for the identification of the role of Gli2 during embryogenesis, growth and development and to the understanding of the function of Gli2 and Shh signaling as involved in basal cell carcinoma in which the gene is responsible and/or related for the testing of possible therapies.

The term "non-human animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration or genetic information, they are transgenic animals as well.

Mice are often used for transgenic animal models because they are easy to house, relatively inexpensive, and easy to breed. However, other non-human transgenic mammals may also be made in accordance with the present invention such as but not limited to monkeys, sheep, rabbits and rats. Transgenic animals are those which carry a transgene, that is, a cloned gene introduced and stably incorporated which is passed on to successive generations. In the present invention, the mouse Gli2 cDNA was cloned and stably incorporated into the genome of a mouse. Alternatively, altered portions of the Gli2 gene sequence may be used. In this manner, the specific function of alternatively spliced gene products may be investigated during animal development and initiation of malignancy in order to develop therapeutic strategies.

There are several methods in which to create a transgenic animal model carrying a certain gene sequence in addition to that specifically provided in the present invention. Generation of a specific alteration of the mouse Gli2 gene sequence is one strategy. Alterations can be accomplished by a variety of enzymatic and chemical methods used in vitro. One of the most common methods is using a specific oligonucleotide as a mutagen to generate precisely designed deletions, insertions and point mutations in a DNA sequence. Secondly, a wild type human gene and/or humanized murine gene could be inserted by homologous recombination. It is also possible to insert an altered or mutant (single or multiple) human gene as genomic or minigene constructs using wild type or mutant or artificial promoter elements. Knock-out of the endogenous murine genes may be accomplished by the insertion of artificially modified fragments of the endogenous gene by homologous recombination. In this technique, mutant alleles are introduced by homologous recombination into embryonic stem cells. The embryonic stem cells containing a knock out mutation in one allele of the gene being studied are introduced into early mouse embryos. The resultant mice are chimeras containing tissues derived from both the transplanted ES cells and host cells. The chimeric mice are mated to assess whether the mutation is incorporated into the germ line. Those chimeric mice each heterozygous for the knock-out mutation are mated to produce homozygous knock-out mice.

Gene targeting producing gene knock-outs allows one to assess in vivo function of a gene which has been altered and used to replace a normal copy. The modifications include insertion of mutant stop codons, the deletion of DNA sequences, or the inclusion of recombination elements (lox p sites) recognized by enzymes such as Cre recombinase. Cre-lox system as used in one embodiment of the present invention allows for the ablation of a given gene or the ablation of a certain portion of the gene sequence. The Cre-lox system was used to generate K5-Cre:Z/APGli2 and K5-Cre:Z/AP-Gli2ΔN mice exhibiting basal cell carcinoma.

To inactivate a gene chemical or x-ray mutagenesis of mouse gametes, followed by fertilization, can be applied. Heterozygous offspring can then be identified by Southern blotting to demonstrate loss of one allele by dosage, or failure to inherit one parental allele using RFLP markers.

To create a transgenic mouse an altered version of the human gene of interest can be inserted into a mouse germ line using standard techniques of oocyte microinjection or transfection or microinjection into stem cells. Alternatively, if it is desired to inactivate or replace the endogenous gene, homologous recombination using embryonic stem cells may be applied as described above.

For oocyte injection, one or more copies of the normal human or mouse Gli2 gene or altered human or mouse Gli2 gene sequence can be inserted into the pronucleus of a just-fertilized mouse oocyte. This oocyte is then reimplanted into a pseudo-pregnant foster mother. The liveborn mice can then be screened for integrants using analysis of tail DNA for the presence of the Gli2 gene sequences. The transgene can be either a complete genomic sequence injected as a YAC or chromosome fragment, a cDNA with either the natural promoter or a heterologous promoter, or a minigene containing all of the coding region and other elements found to be necessary for optimum expression.

Retroviral infection of early embryos can also be done to insert the altered gene. In this method, the altered gene is inserted into a retroviral vector which is used to directly infect mouse embryos during the early stages of development to generate a chimera, some of which will lead to germline transmission (Jaenisch, R. 1976. Proc. Natl. Acad. Sci. USA, 73: 1260–1264).

Homologous recombination using stem cells allows for the screening of gene transfer cells to identify the rare homologous recombination events. Once identified, these can be used to generate chimeras by injection of mouse blastocysts, and a proportion of the resulting mice will show germline transmission from the recombinant line. This gene targeting methodology is especially useful if inactivation of the gene is desired. For example, inactivation of the gene can be done by designing a DNA fragment which contains sequences from an exon flanking a selectable marker. Homologous recombination leads to the insertion of the marker sequences in the middle of an exon, inactivating the gene. DNA analysis of individual clones can then be used to recognize the homologous recombination events.

It is also possible to create mutations in the mouse germlne by injecting oligonucleotides containing the mutation of interest and screening the resulting cells by PCR.

Method of making transgenic mammals are described, e.g., in Wall et al., 1992, J. Cell Biochem June: 49(2), 113–20; Hogan, et al., 1986, in Manipulating the mouse embryo. A Laboratory Manual. Cold Spring Harbor Laboratory Press, Cold Spring Harbor, N.Y. ; in WO 91/08216 or U.S. Pat. No. 4,736,866 the disclosures of which are hereby incorporated by reference. The present invention encompasses a variety of different methods to create a transgenic non-human mammal containing a Gli2 sequence or variant thereof which expression in the mammal leads to the development of basal cell carcinoma. Exemplary and preferred methods are described herein but not intended to limit the scope of the invention.

This embodiment of the invention has the most significant commercial value as an in vivo model for basal cell carcinoma. The role of Gli2 can be identified during growth and development of the transgenic animal to study its expression and effects in skin as well as the epidermal basal layer and outer root sheath of hair follicles with respect to malignancy. Transgenic animals which overexpress Gli2 in skin can now be made and studied with respect to malignancy and used as a model to study possible therapies including pharmaceutical intervention, gene targeting techniques, antisense therapies, antibody therapies etc. Furthermore, transgenic in vitro cell lines can also now be established in accordance with the present invention and also used in order to elucidate intracellular signaling systems involved in the disease as well as test and identify potentially therapeutic compounds.

A preferred in vitro cellular assay for identifying molecular therapeutic compounds or agents is comprised of the steps of: (a) incubating transgenic cells expressing Gli2 with a test compound; and (b) detecting the effect of test compound on Gli2 expression, wherein the detection of an effect indicates that the test compound may be an inhibitor of BCC development.

In other embodiments, cell based assays can be used to identify compounds which modulate expression of a Gli2 gene, modulate translation of a Gli2 mRNA, or which modulate the stability of a Gli2 mRNA or protein. A preferred assay comprises the steps of: (a) incubating a transgenic cell, which expresses a particular Gli2 protein with a test compound; and (b) comparing the amount of the Gli2 protein produced to that produced by the same cell which has not been contacted with the test compound.

In a further embodiment, the effect of a test compound on transcription of a particular Gli2 gene can be determined by a transfection assay, which uses a reporter gene operatively linked to at least a portion of the promoter of a Gli2 gene.

A preferred in vivo assay for identifying a compound which is useful for treating or preventing BCC associated with Gli2 expression is comprised of the steps of a) administering a test compound to a Gli2 transgenic animal; and (b) observing at least one phenotype associated with Gli2 expression, wherein a change in phenotype indicates that the test compound is capable of treating or preventing BCC. The route of administration of the test compound may vary. Example of administration routes include but are not limited to oral, nasal, rectal, transmucosal, intestinal, parenteral, intravenous, and topical. In a preferred embodiment for identifying an effective vaccine, the transgenic non-human animal is made with Gli2 transgene, the compound is a Gli2 antigen or combination of antigens and the phenotype is an immune response.

One skilled in the art would readily comprehend that the nucleic acid construct of the present invention may contain any suitable nucleic acid sequence which encodes for the Gli2 oncogene. Such nucleic acid sequence is preferably the full-length Gli2 cDNA or cDNA encoding for Gli2ΔN (amino acids 280-1544 of the full-length protein) but may encompass other variants or derivatives of such sequence so long as the oncogene is expressed. Nucleic acid variants are those that comprise a sequence substantially different from the Gli2 cDNA sequence but that, due to the degeneracy of the genetic code, still encode Gli2 or Gli2ΔN. The variants may be naturally occurring allelic variants or variants made by recombinant methods particularly art-known mutagenesis techniques. Such nucleic acid variants include those produced by nucleotide substitutions, deletions or additions. The substitutions, deletions or additions may involve one or more nucleotides. Alterations in the coding regions may produce conservative or nonconservative amino acid substitutions, deletions or additions. Especially preferred among these are silent substitutions, additions and deletions which do not alter the properties and activities of the Gli2 oncogene. Nucleotide changes present in a variant polynucleotide are preferably silent, which means that they do not alter the amino acids encoded by the polynucleotide.

One skilled in the art would also understand that the Gli2 gene may be obtained by a wide variety of techniques that include, but are not limited to, isolation from genomic sources, preparation of cDNAs from isolated mRNA templates, direct synthesis, or a combination thereof. These techniques are well known to those of skill in the art. Furthermore, the Gli2 oncogene has been previously described and characterized[7,8,9] and therefore one skilled in the art would readily comprehend what oncogene and sequence is encompassed by reference to the "Gli2" oncogene.

Furthermore, while the invention provides for the use of the bovine keratin 5 (K5) promoter it is understood by those skilled in the art that any suitable promoter element may be used upstream of the Gli2 sequence. Such promoter sequences may include but are not limited to a bone-specific collagen X promoter, a mammary gland-specific murine mammary tumor virus promoter (MMTV), a brain-specific nestin promoter and a βactin promoter. Furthermore, any suitable type of polyA elements can be used downstream of the Gli2 nucleic acid sequence.

The nucleic acid construct of the present invention may also include a regulatory element in order to enhance the expression of the Gli2 transgene. One such regulatory element is the rabbit ℘-globin intron 2 sequence as described herein, however, any similar regulatory elements may also be used such as a CMV enhancer.

EXAMPLES

The examples are described for the purposes of illustration and are not intended to limit the scope of the invention.

Methods of synthetic chemistry, protein and peptide biochemistry, molecular biology, histology and immunology referred to but not explicitly described in this disclosure and examples are reported in the scientific literature and are well known to those skilled in the art.

Example 1

Production of Transgenic Mice

K5-Gli2 Mice

In a first embodiment, a full-length mouse Gli2 cDNA with an amino-terminal FLAG tag was subcloned into the SnaB I site of the bovine K5 transgenic cassette (BK5)[18] using standard techniques, and was verified by DNA sequencing. The BK5 cassette contains 5.3 kb of bovine keratin 5 promoter sequence, rabbit ℘-globin intron 2 sequence, and an SV40 polyA signal. The plasmid insert was purified using a NucleoSpin Kit (Macherey-Nagel, Inc.) and microinjected into fertilized (C57BL/6 X SJL) $F_2$ eggs. K5-Gli2 founders were identified by PCR using primers specific for the rabbit ℘-globin intron (forward 5'-tgcatataaattctggctggcg-3' (SEQ ID NO:1); reverse 5'gcatgaacatggttagcagaggg-3' (SEQ ID NO:2)).

K5-Cre:Z/AP-Gli2N, K5-Cre:Z/AP-Gli2ΔN Mice

In a second aspect of the invention a Cre-loxP based transgenic approach (Z/AP)[32] was used. In brief, this is a binary transgenic system in which the Gli2 transgene was placed downstream of a βgeo (lacZ/neomycin) cassette flanked by a pair of loxP sites (FIG. 4A). For overexpression of Gli2, the Z/AP-Gli2 mice were crossed with a well-characterized K5-Cre transgenic line[30]. The resultant K5-Cre:Z/AP-Gli2ΔN mice develop basal cell carcinoma.

Z/AP-Gli2 and Z/AP-Gli2ΔN mouse lines were also generated by embryonic stem (ES) cell mediated transgenesis. In brief, Gli2 and Gli2ΔN cDNAs[31] were inserted into the pCCALL vector[32] and these constructs were electroporated into ES cells[33]. ES cell clones with high level of lacZ expression were obtained by G418 selection and screened by Xgal-staining. Subsequently, single copy integrations were identified by Southern blot analysis. Cre-dependent expression of the Gli2 and Gli2ΔN transgenes were verified by electroporating Cre into these ES cell clones and immunostaining of epitope-tagged Gli2 and Gli2ΔN using an antibody against the FLAG epitope in the transfected cells (FIG. 4B and data not shown). Chimeric mice were then generated by aggregration of ES cells with morula stage mouse embryos, and Z/AP-Gli2 and Z/AP-Gli2ΔN mouse lines were established after germline transmission[33]. X-gal staining revealed ubiquitous lacZ expression in Z/AP-Gli2 and Z/AP-Gli2ΔN mouse embryos at E10.5 (FIG. 4C and data not shown), and in the adult skin of these mice (FIG. 4D and data not shown).

Animals generated both at the University of Michigan and the Toronto Hospital for Sick Children were handled and housed according to institutional guidelines.

Example 2

Immunohistochemistry

Tissues were fixed overnight in Bouin's fixative or 4% paraformaldehyde (PFA) in PBS, then transferred to 70% ETOH until processing and paraffin-embedding. Immunostaining was performed using eight-micron sections as previously described[29]. Bouin's-fixed tissue sections were used to detect keratins K1, K5, K6, and K17. PFA-fixed sections were used for Bcl-2 immunostaining after boiling in a citrate-based buffer for 10 minutes[29]. Localization of primary antibodies was performed using Vectastain (Vector Labs) and Vectastain Elite kit reagents, and HRP-coupled secondary antibodies with DAB as a substrate. Primary antibodies, dilutions, and sources were as follows: rabbit anti-K1 (1:500); rabbit anti-K5 (1:4000, gift from S. H. Yuspa); rabbit anti-K6 (1:5000); rabbit anti-K17 (1:2000); and rabbit anti-mouse Bcl-2 (1:3000, Pharmingen cat#15616E). Hematoxylin was used as a counterstain.

Example 3

Tumor Harvests and RNA Analysis

Fresh tissue samples were frozen in OCT (Miles) for in situ analysis. Five micron sections were hybridized to biotinylated riboprobes for Gli1, Gli2, and Ptch1 as previously described[14]. RNA was isolated from TriZOL (Life Technologies) homogenates of tumors and skin from age-matched control mice. First-strand cDNA synthesis was performed using SuperScript II RNase H reverse transcriptase with random primers (Life Technologies), and RT-PCR performed using the following primers: FLAG Gli2 (523 bp product) (forward 5'-acaaggacgacgatgacaag-3' (SEQ ID NO:3); reverse 5'agacccctctctttcagatg-3' (SEQ ID NO:4)); Gli1 (364 bp product) (forward 5'-gtcggaagtcctattcacgc-3' (SEQ ID NO:5); reverse 5'-cagtctgctctcttccctgc-3' (SEQ ID NO:6)); Gli2 (326 bp product) (forward 5'-gagcagaagcccttcaag-3' (SEQ ID NO:7); reverse 5'-gacagtcttcacatgctt-3' (SEQ ID NO:8)); Gli3 (275 bp product) (forward 5'-caagcctgatgaagacctcc-3' (SEQ ID NO:9); reverse 5'-gctttgaacggtttctgctc-3' (SEQ ID NO:10)); Ptch1 (243 bp product) (forward 5'-aacaaaaattcaaccaaacctc-3' (SEQ ID NO:11); reverse 5'-tgtcttcaftccagttgatgtg-3' (SEQ ID NO:12)); Ptch2 (200 bp product) (forward 5'-tgcctctctggagggcttcc-3' (SEQ ID NO:13); reverse 5'-cagttcctcctgccagtgca-3' (SEQ ID NO:14)); actin (421 bp product) (forward 5'-taccacaggcattgtgatgga-3 (SEQ ID NO;15); reverse 5'-caacgtcacacftcatgatgg-3' (SEQ ID NO:16)); and Shh (241 bp product) (forward 5'-tctgtgatgaaccagtggcc-3' (SEQ ID NO:17); reverse 5'-gccacggagttctctgctt-3' (SEQ ID NO:18)). Primers were generated based on mouse sequence data. The following PCR parameters were used for Gli1, Gli3, Ptch1, and Shh: 95° C.×50 sec, 58° C.×30 sec, 72° C.×60 sec, for 30 cycles. Deviations from these standard conditions included 35 cycles for amplification of FLAG-Gli2 and Ptch2. For Gli2, the annealing temperature was 54° C. The number of cycles was selected to remain within the linear range of amplification. Reaction products were separated in agarose gels and visualized with ethidium bromide.

It is known that modifications and variations of the present invention as set forth may be made without departing from the spirit and scope thereof. The specific embodiments described herein are given by way of example only and the invention is not limited thereto.

References

1. Landis, S. H., Murray, T., Bolden, S., & Wingo, P. A. Cancer statistics, 1999. CA *Cancer J. Clin.* 49, 8–31, 1 (1999).
2. Dahmane, N., Lee, J., Robins, P., Heller, P., & Ruiz i Altaba, A. Activation of the transcription factor Gli1 and the Sonic hedgehog signalling pathway in skin tumours. *Nature* 389, 876–881 (1997).
3. Unden, A. B., Zaphiropoulos, P. G., Bruce, K., Toftgard, R., & Stahle-Backdahl, M. Human patched (PTCH) mRNA is overexpressed consistently in tumor cells of both familial and sporadic basal cell carcinoma. *Cancer Res.* 57, 2336–2340 (1997).
4. Gailani, M. R. et al. The role of the human homologue of Drosophila patched in sporadic basal cell carcinomas. *Nat Genet.* 14, 78–81 (1996).
5. Hahn, H. et al. Mutations of the human homolog of Drosophila patched in the nevoid basal cell carcinoma syndrome. *Cell* 85, 841–851 (1996).
6. Johnson, R. L. et al. Human homolog of patched, a candidate gene for the basal cell nevus syndrome. *Science* 272, 1668–1671 (1996).
7. Von Ohlen, T., Lessing, D., Nusse, R., & Hooper, J. E. Hedgehog signaling regulates transcription through cubitus interruptus, a sequence-specific DNA binding protein. *Proc. Natl. Acad. Sci. USA* 94, 2404–2409 (1997).
8. Alexandre, C., Jacinto, A., & Ingham, P. W. Transcriptional activation of hedgehog target genes in Drosophila is mediated directly by the cubitus interruptus protein, a member of the GLI family of zinc finger DNA-binding proteins. *Genes Dev.* 10, 2003–2013 (1996).
9. Altaba, A. Gli proteins and hedgehog signaling: development and cancer. *Trends Genet.* 15, 418–425 (1999).
10. Hynes, M. et al. Control of cell pattern in the neural tube by the zinc finger transcription factor and oncogene Gli-1. *Neuron* 19, 15–26 (1997).
11. Lee, J., Platt, K. A., Censullo, P., & Ruiz i Altaba, A. Gli1 is a target of Sonic hedgehog that induces ventral neural tube development. *Development* 124, 2537–2552 (1997).
12. Matise, M. P., Epstein, D. J., Park, H. L., Plaft, K. A., & Joyner, A. L. Gli2 is required for induction of floor plate and adjacent cells, but not most ventral neurons in the mouse central nervous system. *Development* 125, 2759–2770 (1998).
13. Oro, A. E., Higgins, K., & Scott, M. P. Regulation of Shh target gene expression plays a critical role in hair follicle and BCC formation. *J. Invest. Dermatol.* 112, 525 (abstract) (1999).
14. Ding, Q. et al. Diminished Sonic hedgehog signaling and lack of floor plate differentiation in Gli2 mutant mice. *Development* 125, 2533–2543 (1998).
15. Hardcastle, Z., Mo, R., Hui, C. C., & Sharpe, P. T. The Shh signalling pathway in tooth development: defects in Gli2 and Gli3 mutants. *Development* 125, 2803–2811 (1998).
16. Motoyama, J. et al. Essential function of Gli2 and Gli3 in the formation of lung, trachea and oesophagus. *Nat Genet* 20, 54–57 (1998).
17. Lavker, R. M. et al. Hair follicle stem cells: their location, role in hair cycle, and involvement in skin tumor formation. *J. Invest Dermatol.* 101, 16S-26S (1993).
18. Ramirez, A., Bravo, A., Jorcano, J. L., & Vidal, M. Sequences 5' of the bovine keratin 5 gene direct tissue- and cell-type- specific expression of a lacZ gene in the adult and during development. *Differentiation.* 58, 53–64 (1994).
19. McGowan, K. M. & Coulombe, P. A. Onset of keratin 17 expression coincides with the definition of major epithelial lineages during skin development. *J. Cell Biol.* 143, 469–486 (1998).
20. Markey, A. C., Lane, E. B., MacDonald, D. M., & Leigh, I. M. Keratin expression in basal cell carcinomas. *Br. J. Dermatol.* 126,154–160 (1992).
21. Smoller, B. R., van de Rijn, M., Lebrun, D., & Warnke, R. A. bcl-2 expression reliably distinguishes trichoepitheliomas from basal cell carcinomas. *Br. J. Dermatol.* 131, 28–31 (1994).
22. Yoshikawa, K., Katagata, Y., & Kondo, S. Biochemical and immunohistochemical analyses of keratin expression in basal cell carcinoma. *J. Dermatol. Sci.* 17,15–23 (1998).
23. Nagano, T. et al. Overexpression of the human homologue of Drosophila patched (PTCH) in skin tumours: specificity for basal cell carcinoma. *Br. J. Dermatol.* 140, 287–290 (1999).
24. Kallassy, M. et al. Patched (ptch)-associated preferential expression of smoothened (smoh) in human basal cell carcinoma of the skin. *Cancer Res.* 57, 4731–4735 (1997).
25. Green, J., Leigh, I. M., Poulsom, R., & Quinn, A. G. Basal cell carcinoma development is associated with induction of the expression of the transcription factor Gli-1. *Br. J. Dermatol.* 139, 911–915 (1998).
26. Oro, A. E. et al. Basal cell carcinomas in mice overexpressing sonic hedgehog. *Science* 276, 817–821 (1997).
27. Xie, J. et al. Activating Smoothened mutations in sporadic basal-cell carcinoma. *Nature* 391, 90–92 (1998).
28. Aszterbaum, M. et al. Ultraviolet and ionizing radiation enhance the growth of BCCs and trichoblastomas in patched heterozygous knockout mice. *Nat. Med.* 5, 1285–1291 (1999).
29. Chiang, C. et al. Essential role for sonic hedgehog during hair follicle morphogenesis. *Dev.Biol.* 205, 1–9 (1999).
30. Tarutani, M., Itami, S., Okabe, M., Ikawa, M., Tezuka, T., Yoshikawa, K., Kinoshita, T., and Takeda, J. Tissue-specific knockout of the mouse Pig-a gene reveals important roles for GPI-anchored proteins in skin development. Proc. Natl. Acad. Sci. USA 94: 7400–7405,1997.
31. Sasaki, H., Nishizaki, Y., Hui, C.C., Nakafuku, M., and Kondoh, H. Regulation of Gli2 and Gli3 activities by an amino-terminal repression domain: implication of Gli2 and Gli3 as primary mediators of Shh signaling. Development, 126: 3915–3924, 1999.
32. Lobe, C. G., Koop, K. E., Kreppner, W., Lomeli, H., Gertsenstein, M., and Nagy, A. Z/AP, a double reporter for Cre-mediated recombination. Dev. Biol., 208: 281–292, 1999.
33. Mo, R, Freer AM, Zinyk DL, Crackower MA, Michaud J, Heng HH-Q, Chik KW, Shi X-M, Tsui L-C, Cheng SH, Joyner AL, Hui C. C. Specific and redundant functions of Gli2 and Gli3 zinc finger genes in skeletal patterning and development. *Development* 124,113–123, 1997.

That which is claimed is:

1. A transgenic mouse whose genome comprises a transgene comprising a nucleotide sequence encoding a full-length mouse Gli2 operably linked to a bovine keratin 5 (K5) promoter, wherein full-length Gli2 is expressed and said transgenic mouse develops basal cell carcinoma.

2. The transgenic mouse of claim 1, wherein said basal cell carcinoma is characterized by expression of keratin 17 (K17), Bcl-2, keratin K5 and lack of expression of keratin K1 and keratin 6.

3. The transgenic mouse of claim 2, wherein said basal cell carcinoma is further characterized by elevated levels of Ptch1 and Gli1.

4. The transgenic mouse of claim 1 wherein said nucleotide sequence is a Gli2 cDNA sequence.

5. A cell isolated from the transgenic mouse of claim 1, wherein said cell expresses said transgene and is a keratinocyte.

6. A keratinocyte cell line derived from the transgenic mouse of claim 1, wherein cells of said keratinocyte cell line express said transgene.

7. The transgenic mouse of claim 1, wherein said transgenic mouse is fertile and transmits said transgene to its offspring.

8. A method of generating the transgenic mouse of claim 1, comprising, introducing a transgene comprising a nucleotide sequence encoding a full-length mouse Gli2 operably linked to a bovine keratin 5 (K5) promoter into a mouse fertilized oocyte, allowing said fertilized oocyte to develop into an embryo, transferring said embryo into a pseudopregnant female mouse, allowing said embryo to develop to term, and identifying said transgenic mouse.

9. A method of identifying an agent for treating basal cell carcinoma comprising, providing two transgenic mice according to claim 1, administering an agent to one said transgenic mouse, comparing the basal cell carcinoma in the transgenic mouse to which an agent has been administered with the basal cell carcinoma of the other transgenic mouse to which the agent has not been administered, wherein an agent that reduces the basal cell carcinoma is identified as an agent that treats basal cell carcinoma.

* * * * *